United States Patent [19]

Craig et al.

[11] Patent Number: Plant 7,467

[45] Date of Patent: Mar. 12, 1991

[54] REGAL PELARGONIUM 'ALLURE'

[75] Inventors: Richard Craig, State College, Pa.; Glenn G. Hanniford, Worthington, Ohio

[73] Assignee: Research Corporation Technologies, Tucson, Ariz.

[21] Appl. No.: 337,781

[22] Filed: Apr. 10, 1989

[51] Int. Cl.[5] ..... A01H 5/00

[52] U.S. Cl. ..... Plt./68

[58] Field of Search ..... Plt./68

[56] References Cited

PUBLICATIONS

*Penn Stater News*, "Photo of New Geranium to Appear on University Greeting Card", Dec. 1, 1988.

Penn State News Bureau, *Centre Daily Times*, "Geranium Chosen for Holiday Card", B-2, Dec. 11, 1988.

Peterson, *Penn Stater*, "Research Blossoms in Regal Debut", Penn State Alumni Association: 9-10, Jan.-/Feb. 1989.

Greeting Card-Regal Geraniums "Crystal" series, developed by Dr. Richard Craig and Dr. Glenn G. Hanniford.

Craig, *Grower Expo*, "Star Wars Approach to Designing the Perfect Regal Geranium", 1989.

*Primary Examiner*—Howard J. Locker

*Attorney, Agent, or Firm*—Scully, Scott, Murphy, & Presser

[57] ABSTRACT

This invention relates to a new and distinct cultivar of regal Pelargonium (*Pelargonium*×*domesticum*) named 'Allure' substantially as illustrated and described herein, particularly characterized as being compact and self-branching, early flowering, and having flowers which are soft pink in color with red feathering on the upper two petals thereof.

2 Drawing Sheets

The present invention relates to a new and distinct cultivar of regal Pelargonium (*Pelargonium*×*domesticum*) called 'Allure'. This cultivar is compact and self-branching (without pinching) and early flowering. The flowers are soft pink with red feathering on the upper two petals.

The cultivar was developed from an organized, scientifically designed breeding program conducted at the Department of Horticulture, The Pennsylvania State University, University Park, Pa. 16802. The objective was to produce a new regal Pelargonium genotype with excellent propagation characteristics, compact growth habit, predictable and consistent flowering response and good postharvest quality. 'Allure' resulted from the selection from the progeny of the cross-pollination of regal Pelargonium cultivars 'White Glory' and 'Melissa'. The selection was asexually propagated by cuttings and the reproductions ran true.

Figure 1:
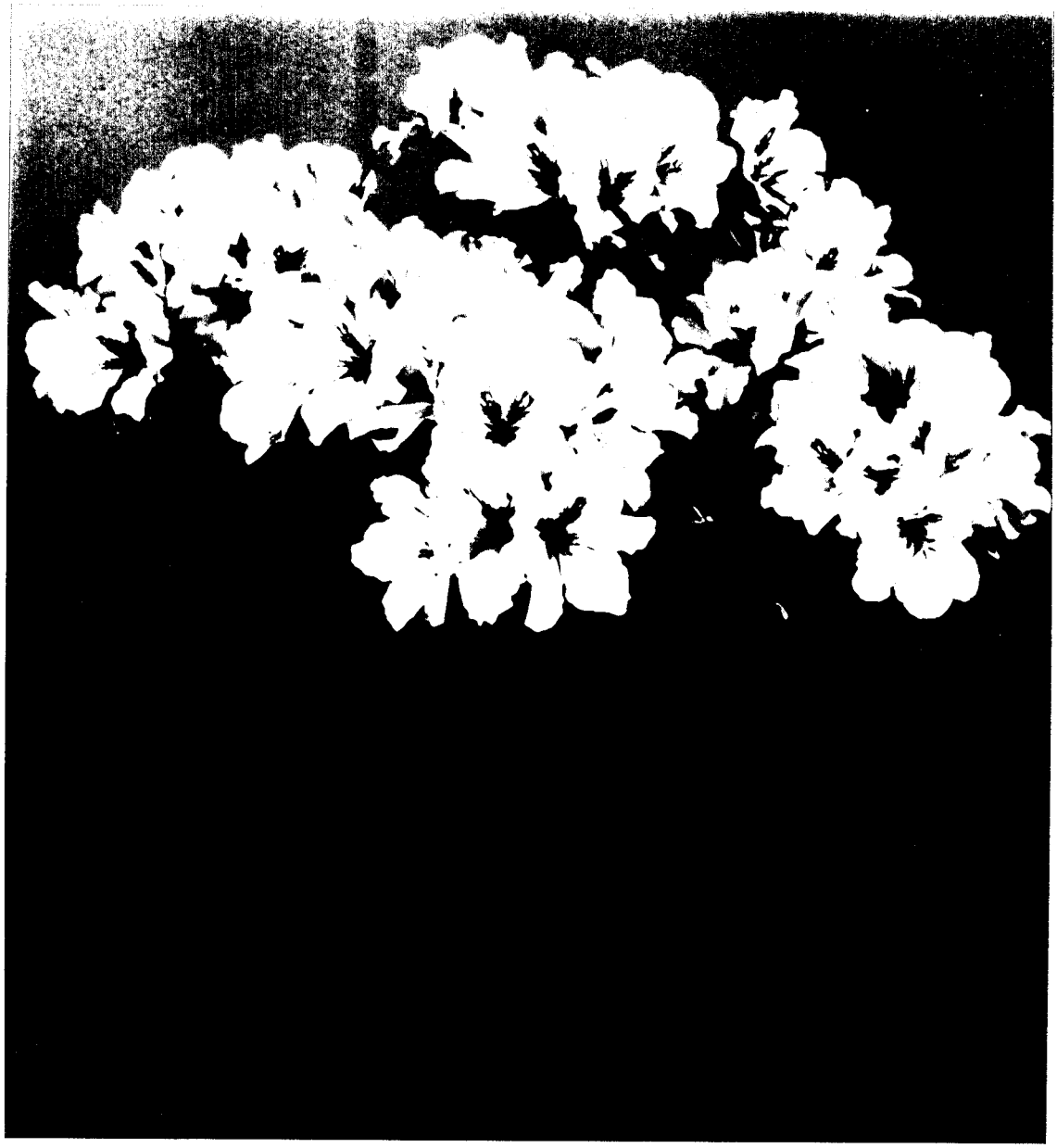
FIG. 1 illustrates in color the cultivar (cultivated with pinching) including foliage and flowers.
Figure 2:
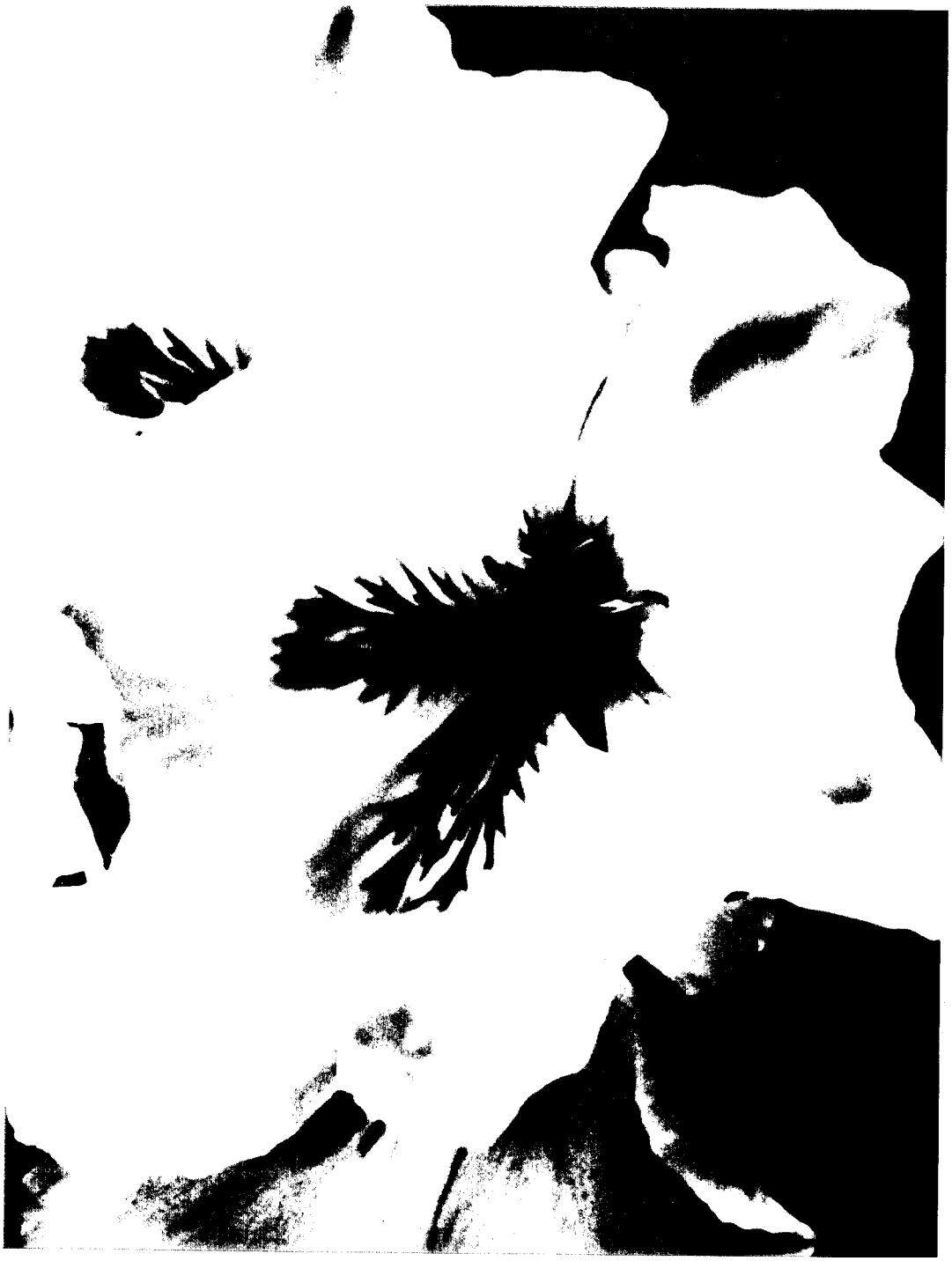
FIG. 2 illustrates in color primarily the floret.

With reference to the detailed description of the cultivar which follows, the test plant was potted in soilless medium and grown in a glasshouse under natural sunlight at a night temperature of approximately 58° F. and a day temperature of approximately 68° F. Fertilizer was applied in every watering, with 200 ppm nitrogen provided in the forms of 15-16-17 (two consecutive waterings) and 20-0-20 (every third watering) in a repeating cycle.

Color readings were taken under incandescent light at approximately 200 foot candles and color identification was by reference to the Royal Horticultural Society Colour Charts, except where common terms of color definition are employed.

THE PLANT

Classificationn:

*Botanical.*—*Pelargonium*×*domesticum.*

*Tradename.*—#30-(81-59-1)='Allure'.

Form: Compact, self-branching.

Height: 14–25 cm [will vary with environmental and cultural conditions].

Leaves:

*Size.*—Largest leaf measured 8.0 cm long×12.0 cm wide.

*Shape.*—Depressed ovate; base is cuneate to truncate to reniform; variously lobed; ratio of length to width is 2 to 3.

*Margin.*—Toothed.

*Texture.*—Pubescent.

*Color.*—Adaxial: Green 137C. Abaxial: Green 138A.

*Ribs and veins.*—Palmate venation.

*Petioles.*—Texture: Lightly pubescent. Length: Up to 7.5 cm. Color: Yellow-green 144A.

Stem:

*Internode length.*—Up to 3.5 cm.

*Color.*—Yellow-green 144A.

THE FLOWER

Blooming habit: Early; inflorescence number comparable to the cultivar 'Grand Slam'.

Inflorescence form: Umbellate.

Inflorescence size: Varies with floret number; often 9.0–13.0 cm across (with florets fully open).

Disease resistance: Not known.

Florets:

*Number.*—Up to 8 per inflorescence.

*Form.*—Cupped.

*Size.*—5.0–6.0 cm across open floret.

Petals:

*Number.*—5–8.

*Texture and appearance.*—Smooth, with slightly wrinkled margins.

*Color.*—Upper petals: Adaxial: Margin: Red-purple 62A. Central spot: Greyed-purple 187A with narrow red 42A halo. Proximal veins and feathering: Greyed-purple 187A. Base: White 155A. Abaxial: Margin: Red-purple 62D. Central spot, proximal veins and feathering: Red-purple 64A; spot smaller than adaxial spot. Lower petals: Adaxial: Red-purple 62A. Basal veins: Red-purple 61A. Base: White 155A. Abaxial: Red-purple 62D. Basal veins: Red-purple 61D.

Petaloids:

*Number.*—0 or 1.

*Shape.*—Petal-like (but sometimes fused with a sepal).

*Color.*—Similar to the color of the petals.

Sepals:

*Number.*—5–7.

Pedicel: Subtended by bracts.

*Length.*—Up to 4.8 cm.

*Color.*—Yellow-green 144A.

Peduncle: Arises from node; opposed to leaf petiole; subtended by leaves and bracts.

*Length.*—Up to 9.5 cm.

*Color.*—Yellow-green 144B.

REPRODUCTIVE ORGANS

Androecium:

*Stamens.*—7–10 flat, ribbon-like filaments, joined at their bases; upper ⅓ of filaments is light purple; versatile attachment to anthers which are light purple and well developed; 2 sizes of orange pollen.

*Staminodes.*—1–4 flat, ribbon-like filaments with no anthers.

*Petaloid stamens.*—None observed.

Gynoecium:

*Pistil number.*—1.

*Length.*—16.0–24.5 mm.

*Stigma.*—5–6-parted; purple.

*Style.*—7.0–13.5 mm long; purple.

*Ovary.*—5.5–6.5 mm long; superior; very pubescent.

Fruit: Schizocarp; rarely observed.

What is claimed is:

1. A new and distinct cultivar of regal Pelargonium substantially as illustrated and described herein, particularly characterized as being compact and self-branching, early flowering, and having flowers which are soft pink in color with red feathering on the upper two petals thereof.

* * * * *

UNITED STATES PATENT AND TRADEMARK OFFICE

CERTIFICATE OF CORRECTION

PATENT NO. : Plant 7,467

DATED : March 12, 1991

INVENTOR(S) : Richard Craig, et al.

It is certified that error appears in the above-identified patent and that said Letters Patent is hereby corrected as shown below:

Column 1, lines 2 & 17: "Pelargonium" should read as --pelargonium--

Column 2, line 3: "Classificationn" should read as --Classification--

Column 4, line 22, Claim 1: "Pelargonium" should read as --pelargonium--

Signed and Sealed this

Twenty-fourth Day of November, 1992

*Attest:*

DOUGLAS B. COMER

*Attesting Officer*

*Acting Commissioner of Patents and Trademarks*